United States Patent [19]

Vincent et al.

[11] Patent Number: 5,422,362
[45] Date of Patent: Jun. 6, 1995

[54] METHOD TO INHIBIT RESTENOSIS

[75] Inventors: G. Michael Vincent, Salt Lake City, Utah; Patricia M. Logan, Vancouver, Canada

[73] Assignee: Quadra Logic Technologies, Inc., Vancouver, Canada

[21] Appl. No.: 99,210

[22] Filed: Jul. 29, 1993

[51] Int. Cl.⁶ ............................................. A61K 31/40
[52] U.S. Cl. .................................................... 514/410
[58] Field of Search ......................................... 514/410

[56] References Cited

U.S. PATENT DOCUMENTS

| | | | |
|---|---|---|---|
| 5,116,864 | 5/1992 | March et al. | 514/455 |
| 5,283,255 | 2/1994 | Levy et al. | 514/410 |
| 5,308,608 | 5/1994 | Dolphin et al. | 514/410 |
| 5,308,861 | 5/1994 | Aizawa et al. | 514/410 |
| 5,314,905 | 5/1994 | Pandey et al. | 514/410 |

OTHER PUBLICATIONS

Sobeh, M. S. et al., *Vascular Surgical Society of Great Britain and Ireland Annual General Meeting*, London, Nov. 1992.
Sobeh, M. S. et al., *13th Annual American Society of Laser Medicine and Surgery*, New Orleans, Apr. 1993.
Copperath, K. et al., *Eur. Heart. J.* (1989) 10 (Suppl):151.
Asahara, T. et al., *Circulation* (1992) 86(Suppl) I–846.
Kessel, D. et al., "Porphyrin Accumulation by Atheromatous Plaques of the Aorta", *Photochem. Photobiol.* (1984) 40:59–61.
Okunaka, T. et al., "Hematoporphyrin Derivative Uptake by Atheroma in Atherosclerotic Rabbits: The Spectra of Fluoresence from Hematoporphyrin Derivatives Demonstrated by an Excimer Dye Laser", *Photochem. Photobiol.* (1987) 46:769–775.
Spears, J. et al., "Fluorescence of Experimental Atheromatous Plaques with Hematoporphyrin Derivative", *J. Clin. Invest.* (1983) 71:395–399.
Spokojny, A. et al., "Uptake of Hematoprphyrin Derivative by Atheromatous Plaques: Studies in Human in Vitro and Rabbit in Vivo", *J. Am. Col. Cardiol.* (1986) 8:1387–1392.
Straight, R. et al., "Porphyrin Retention and Photodynamic Treatment of Diet Induced Atherosclerotic Lesions in Pigs", *Photodynamic Therapy of Tumors and Other Diseases*, (1985) pp. 349–352.
Dartsch, P. eta l., "Photodynamic Therapy of Vascular Stenoses? III–10", *Advances in Laser Medicine 4: Laser Angioplasty II* (Biamino, G., et al. eds. 1990) Ecomed Verlagsgesellschaft, Landsberg/Lech, Berlin 77–80.
Dartsch, P. et al., "Differential Effect of Photofrin II on Growth of Human Smooth Muscle Cells from Nonatherosclerotic Arteries and Atheromatous Plaques in Vitro", *Atherosclerosis* (1990) 10:616–624.
Dartsch, P. et al., "Responses of Cultured Smooth Muscle Cells From Human Nonatherosclerotic Arteries and Primary Stenosing Lesions After Photoradiation: Implications for Photodynamic Therapy of Vascular Stenoses", *J. Am. Coll. Cardio.* (1990) 15:1545–1550.
Ortu, P. et al., "Photodynamic Therapy of Arteries", *Circulation* (1992) 85:1189–1196.
Eton, D. et al., "Inhibition of Intimal Hyperplasia by Photodynamic Therapy Using Photofrin", *J. Surg. Res.* (1992) 53:558–562.

*Primary Examiner*—James H. Reamer
*Attorney, Agent, or Firm*—Morrison & Foerster

[57] ABSTRACT

A method to inhibit the development of intimal hyperplasia following vascular intervention procedures (angioplasty) is disclosed. The method consists essentially of administering a green porphyrin to the subject concurrent with and following the angioplasty. No purposeful irradiation with light absorbed by the green porphyrin is required or employed in the method.

22 Claims, 2 Drawing Sheets

FORMULA 1

FORMULA 2

FORMULA 3

FORMULA 4

FORMULA 5

FORMULA 6

METHOD TO INHIBIT RESTENOSIS

TECHNICAL FIELD

The invention concerns methods to prevent development of restenosis or intimal hyperplasia. This process is a commonly occurring side effect of angioplasty. More specifically, the invention concerns inhibition of restenosis by administering a green porphyrin to the angioplasty subject roughly concurrently with the angioplasty procedure and for several months following the procedure. No purposeful irradiation with light is needed to effect the desired inhibition.

BACKGROUND ART

Invasive manipulation of the peripheral circulatory system to correct occlusive diseases of the arteries has become more and more routine. Over 200,000 procedures are performed annually in the United States alone which involve blood vessel bypasses, balloon catheters, and other "mechanical" techniques to correct the problem. A serious side effect of these procedures is the subsequent development in the subject of intimal hyperplasia which may, itself, constitute a blockage problem. This appears to be a direct response to the intimal injury caused by the intervention; smooth muscle cells and fibroblasts proliferate and create stenoses in the interior of the vascular wall. The mechanism of this process is evidently not well understood, but a central feature of the development of the problem appears to be unwanted proliferation of smooth muscle cells.

Various methods have been tried to overcome this dangerous side effect. Approaches have included mechanical manipulation as well as administration of chemical agents such as aspirin, dexamethasone, heparins, calcium channel blockers, and a variety of other agents presumed on the basis of various theories to interfere with the development of the stenoses. They have met with very little success and have side effects of their own.

One additional approach is the use of photodynamic therapy (PDT). This form of management, originally applied to cancer treatment, involves the use of photoactive materials which home to tumor tissue, presumably because of the rapidly proliferating nature of the tissue. The photoactive substances, which include psoralen, various porphyrin-based materials, such as Photofrin II ™ porphyrin aggregate, chlorins, phthalocyanins, and monohydrobenzoporphyrin derivatives, to name but a few, are harmless unless photoactivated. However, when irradiated with light of appropriate wavelength, the drugs apparently effect the formation of a toxic agent, presumably singlet oxygen, although they themselves are chemically unchanged. The resultant toxic agent causes the destruction of the unwanted tumor tissue.

PDT has also been applied with some success to the treatment of atherosclerotic plaques. See, for example, Kessel, D. et al., *Photochem Photobiol* (1984) 40:59–62; Okunaka, T. et al., *Photochem Photobiol* (1987) 46:769–775; Spears, J. R. et al., *J Clin Invest* (1983) 71:395–399; Spokqiny, A. M. et al., *J Am Col Cardiol* (1986) 8:1387–1392; Copperath, K. et al., *Eur Heart J* (1989) 10 (Suppl):151; Straight, R. et al., *Photodynamic Therapy of Tumors and Other Diseases*, (1985) pp. 349–350.

The use of PDT to treat or prevent the restenosis that often accompanies angioplasty has also been studied. These studies have either employed smooth muscle cells in (SMC) in culture, on the theory that SMC proliferation is the sine qua non of restenosis, or have used animal models. In general, PDT appears to show promise in this regard. However, controls run in many of these studies, using the photoactivating agent in the absence of light, have provided contradictory results when smooth muscle cells in culture were used as the model system. Applicants are unaware of any animal studies which showed any indication of positive results for preventing restenosis in the absence of light.

Dartsch, P. C. et al. reported in Advances in Laser Medicine 4: *Laser Angioplasty II* Biamino, G., et al. (ads) Ecomed Verlagsgesellschaft, Landsberg/Lech, Berlin (1990) 77–80, the results of contracting smooth muscle cells in culture exposed to dihematoporphyrin-ester and -ether (DHE). This porphyrin-based drug is now marketed as Photofrin II ™. The report discloses that SMC were isolated by enzymatic disaggregation of either normal or stenosing plaque tissues and cultured in vitro. They were tested in their first, second or third passage by treating them with DHE at concentrations ranging from 0.1–25 $\mu$g/ml and irradiated with ultraviolet light. The percentage of viable and still adherent cells was markedly reduced for plaque-derived SMC and much less dramatically reduced for normal SMC. A less dramatic, but nevertheless detectable, effect was observed in the presence of DHE but in the absence of radiation. Specifically, cells treated with 5 $\mu$g/ml DHE and light showed a reduction in the number of viable cells to 73% in the case of normal derived cells and 38% for plaque-derived SMC. Using a DHE concentration of 1 $\mu$g/ml and an energy density of 1200 mJ/cm2, after 24 hours 80% of the normal SMC and 20% of the plaque-derived SMC were viable. Similar results were reported by this group in related publications: Dartsch, P. C. et al., *Atherosclerosis* (1990) 10:616–624; Dartsch, P. C. et al., *J Am Coll Cardiol* (1990) 15:1545–1550.

In two recent reports by Sobeh, M. S. et al., results apparently contradictory to those of Dartsch, et al. were obtained when SMC cultured from the intermedia of human long saphenous vein harvested for coronary artery vein bypass grafting, were used in the tests. These cells were treated with Photofrin II ™ porphyrin aggregates and irradiated. These reports state that the cells were unaffected by Photofrin II ™ porphyrin aggregate at 0–100 $\mu$g/ml without light. However, when treated with light energy of greater than 3 J/cm2 in the presence at least 2 $\mu$g/ml of the drug, a mean cell destruction of over 80% was reported regardless of wavelength. The reports also state that light without prior chromophore sensitization produced no cell damage. (Vascular Surgical Society of Great Britain and Ireland Annual General Meeting, London, November 1992; 13th Annual American Society of Laser Medicine and Surgery, New Orleans, April 1993.)

Asahara, T. et al. reported in *Circulation* (1992) 86 (Suppl) 1–846, that PDT was able to inhibit restenosis in rabbits that had received balloon injuries of the iliac artery and were fed with a 0.2% cholesterol diet. Hematoporphyrin derivative (HPD) was administered 24 hours before irradiation at various times relative to the injury. The best effects were observed when the treatment was administered one week after angioplasty.

In another in vivo study, Ortu, P. et al., *Circulation* (1992) 85:1189–1196, reported that photodynamic therapy, with chloraluminum-sulfonated phthalocyanine (CASPc) used as the drug, was effective in inhibiting the intimal hyperplasia response in rats subjected to balloon injury of the carotid artery. Controls consisted of rats irradiated, but not administered the drug. No controls using CASPc without light were reported.

Eton, D. et al., *J. Surg. Res.* (1992) 53:558–562, reported the effect of photodynamic therapy using Photofrin II ™ porphyrin aggregates in a rabbit model wherein the rabbits underwent standardized intimal injury to both common carotid arteries with a balloon catheter. The test animals received Photofrin II ™ porphyrin aggregate and subsequent irradiation; the control groups either received no treatment, or chromophore alone, or light alone. The results were evaluated in terms of arterial cross sections. Only the test group showed a statistically significant improvement over the controls, although the animals treated with light alone or Photofrin II ™ porphyrin aggregate alone had non-significant lower mean ratios of the area of intimal hyperplasia to the area enclosed by the internal elastic lamina, used as a measure of stenosis in this study.

It would be advantageous to provide a treatment to prevent intimal hyperplasia (IH) following vascular trauma which is independent of PDT, so that the necessity to provide light using specialized equipment is avoided. It has now been found that green porphyrins, administered concurrently with, and for a period of time after, angioplastic procedures, can effectively inhibit the undesired stenoses often accompanying this procedure.

Disclosure of the Invention

The invention provides a method to prevent or inhibit the intimal hyperplasia and resultant restenosis which occur as side effects of corrective vascular treatments. The method comprises administering to a subject undergoing an angioplasty, concurrently with this procedure, an amount of green porphyrin effective to interfere with the development of restenosis. The administration of the drug need not be accompanied by purposeful irradiation with light; indeed, the treatment is performed without irradiation by light absorbed by the green porphyrin administered.

Thus, in summary, the invention is directed to a method to inhibit the development of intimal hyperplasia following angioplasty, which method consists essentially of administering to a subject, in conjunction with said angioplasty, an amount of green porphyrin (Gp) effective to inhibit said development, and allowing said inhibition to occur in the absence of purposeful irradiation with light absorbed by the Gp.

MODES OF CARRYING OUT THE INVENTION

The method of the invention is intended to prevent the undesired side effects of angioplasty. As used herein, "angioplasty" refers to surgical procedures which traumatize the vascular walls. Such procedures include, but are not limited to, femoral-popliteal bypasses, femoral-tibial bypasses, aorto-iliac bypasses, coronary bypasses, percutaneous transluminal angioplasty, balloon angioplasty, laser angioplasty and directional atherectomy. Any procedure which involves traumatic manipulation of the vasculature is included in this definition.

As used herein, intimal hyperplasia (IH) is defined as a pathophysiological phenomenon which results in the occlusion of the vasculature and is accompanied by the proliferation of cells including smooth muscle cells at the interior of the blood vessels. It is not implied by this definition that the method of the invention necessarily directly inhibits the proliferation of SMC; however, the condition which the method of the invention is designed to inhibit includes such proliferation.

By "in conjunction with angioplasty" is meant application of the method beginning at a time roughly accompanying the angioplastic procedure. This may include multiple or single treatments in the ensuing days, weeks or months after the procedure is performed. "In conjunction with" refers to a time period within the ambit of the effects of the angioplasty procedure. Typically, an initial dose of green porphyrin will be within 6–12 hours of the angioplasty, preferably within 6 hours thereafter. Follow-up dosages may then be made at weekly, biweekly, or monthly intervals. Design of particular protocols depends, of course, on the individual subject, the condition of the subject, the design of the dosage levels, and the judgment of the attending practitioner.

The green porphyrins useful in the method of the invention are described in detail in the issued U.S. Pat. No. 5,171,749 which is incorporated herein in its entirety by reference. These compounds are porphyrin derivatives obtained by reacting a porphyrin nucleus with an alkyne in a Diels-Alder type reaction to obtain a monohydrobenzoporphyrin. Preferred embodiments of the Gp are those wherein the resulting Diels-Alder product is rearranged and partially hydrolyzed. A particularly preferred set of embodiments is designated in the referenced patent as BPD-DA, -DB, -MA, and -MB. Particularly preferred and exemplified herein is BPD-MA.

The Green Porphyrins

Figure 1:
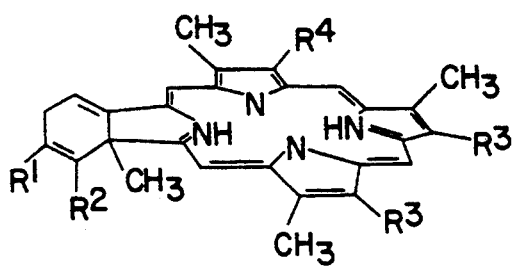
FIG. 1 shows the formulas of typical green porphyrins useful in the invention method.
Figure 1:
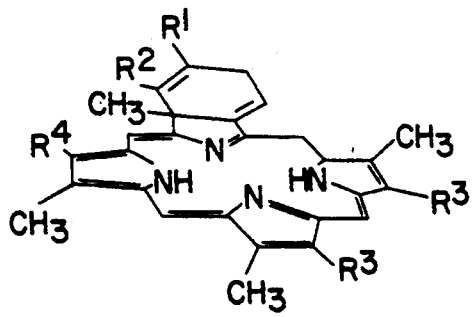
Figure 1:
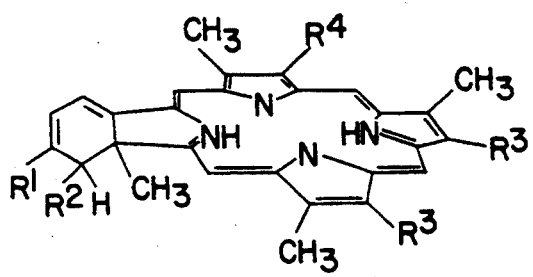
Figure 1:
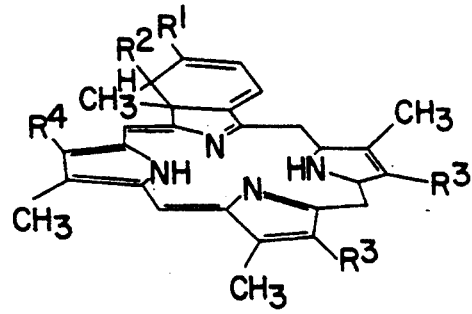
Figure 1:
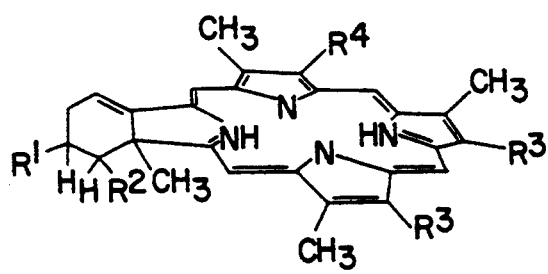
Figure 1:
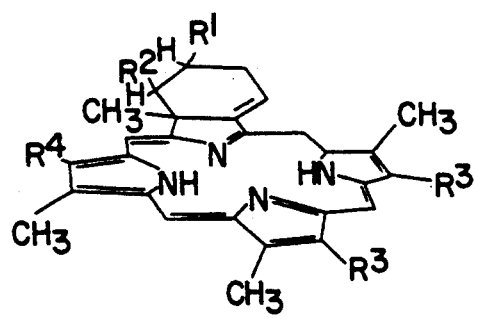
Figure 2:
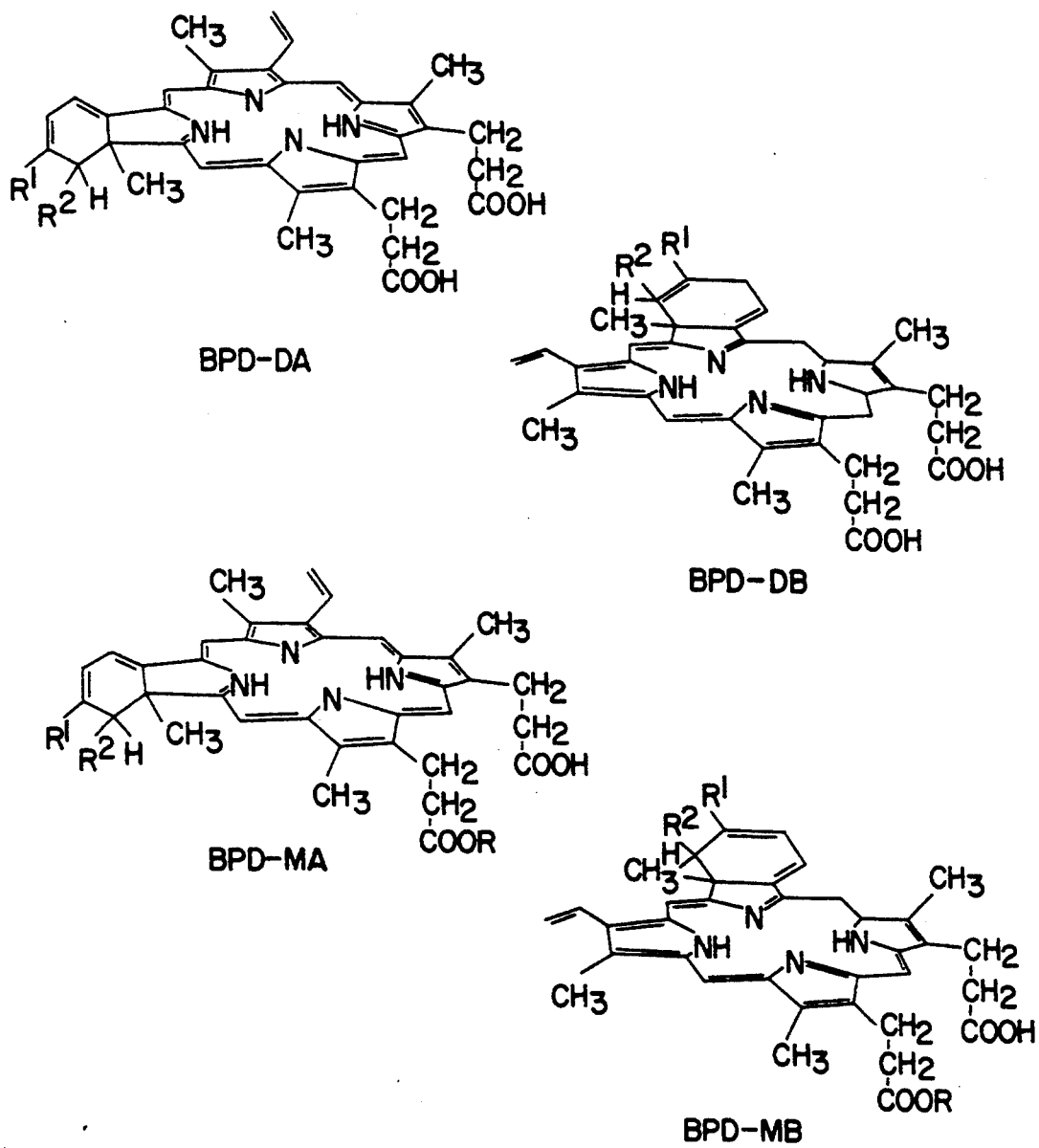
FIG. 2 shows the formulas of 4 particularly preferred embodiments of the green porphyrins of the invention, BPD-DA, BPD-DB, BPD-MA, and BPD-MB.

In further detail with respect to the green porphyrins useful in the invention, the general structures of typical green porphyrins are shown in FIG. 1. Particularly preferred forms are shown in FIG. 2.

Gp is selected from a group of porphyrin derivatives obtained using Diels-Alder reactions of acetylene derivatives with protoporphyrin under conditions which effect a reaction at only one of the two available conjugated, nonaromatic diene structures present in the protoporphyrin-IX ring system (rings A and B). The formulas shown in FIG. 1 represent typical green porphyrins useful in the invention. These compounds are shown in the figure with hydrogen occupying the internal ring nitrogens; however, it is understood that the metalated forms wherein a cation replaces one or both of these hydrogens can also be employed. It is also understood that these compounds can be labeled either by replacement of one or more of the atoms in the structure by its radioactive form, or by coupling to a radioisotope such as a radioactive metal or, for example, a radioisotope of iodine.

For convenience, an abbreviation of the term hydromonobenzoporphyrin derivative —"BPD"—is generally used to refer to compounds of formulas 3 and 4 of FIG. 1. These are the preferred forms of Gp. As shown in FIG. 1, $R^1$, $R^2$, $R^3$ and $R^4$ are non-interfering substituents which do not affect, appreciably, the activity of the compound in the invention method. Most typically, $R^1$ and $R^2$ are carbalkoxy groups, typically methyl or ethyl carboxy esters. Most commonly $R^3$ is 2-carboxyethyl or the alkyl ester thereof and $R^4$ is vinyl. These preferred embodiments result from the availability of native porphyrins and are not mandated by considerations of biological efficacy. By "non-interfering substituents" is meant substituents which do not destroy the ability of the green porphyrin to inhibit hyperplasia.

Dimeric forms of the Gp and dimeric and multimeric forms of Gp/porphyrin combinations can also be employed.

"Green porphyrin" refers to a porphyrin nucleus modified, for example, by a Diels-Alder reaction involving the conjugated system comprising a pyrrole nucleus and a vinyl substituent with an acetylene dienophile. This results in a fused cyclohexadiene—referred to herein as "hydrobenzo"—fused to the A or B ring, as shown in formulas 1 and 2. Rearrangement of the $\pi$ system in the hexadiene ring results in the compounds of formulas 3 and 4; reduction provides the compounds of formulas 5 and 6. Specific preparation of this class of Gp compounds useful in the invention is described in detail in U.S. Pat. No. 5,095,030 incorporated herein by reference.

For the compounds shown in FIGS. 1 and 2, generally, $R^1$ and $R^2$ are each, independently, moderate electron-withdrawing substituents, and are, most commonly, carbalkoxy, alkyl or aryl sulfonyl, or any other activating substituents which are not sufficiently electron-withdrawing to result in reaction with both A and B rings rather than reaction with only one. One of $R^1$ and $R^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl; carboxyalkyl refers to the substituent —R'—COOH wherein R' is alkylene; carbalkoxyalkyl refers to —R'—COOR wherein R' and R are alkylene and alkyl respectively. Alkyl is a saturated straight or branched chain hydrocarbyl of 1–6 carbon atoms such as methyl, n-hexyl, 2-methylpentyl, t-butyl, n-propyl, and so forth. Alkylene is as alkyl except that the group is divalent. Aryl or alkyl sulfonyl moieties have the formula $SO_2R$ wherein R is alkyl as above-defined, or is aryl, wherein aryl is phenyl optionally substituted with 1–3 substituents independently selected from halo (fluoro, chloro, bromo or iodo), lower alkyl (1–4C) or lower alkoxy (1–4C). In addition, one or both $R^1$ of $R^2$ can itself be aryl—i.e., phenyl optionally substituted as above defined.

As shown in FIG. 1, the adduct formed by the reaction of $R^1$—C≡C—$R^2$ with the protoporphyrin-IX ring system ($R^3$ is a protected form of 2-carboxyethyl such as 2-carbomethoxyethyl or 2-carboethoxyethyl; $R^4$ is CH=CH$_2$) are compounds of the formulas 1 and 2 wherein the compound in formula 1 results from addition to the A ring and formula 2 results from addition to the B ring. In these resulting products of formulas 1 and 2, $R^4$ remains CH=CH$_2$, however this vinyl group is readily derivatized to other embodiments of $R^4$ by addition to or oxidation of the vinyl ring substituent of ring B in formula 1 or ring A in formula 2. The addition or oxidation products can be further substituted if the added substituents are functional leaving groups—for example—Br may be substituted by —OH, —OR (R is alkyl 1–6C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. The product of the Markonikov addition of water provides a substituent structure analogous to the hematoporphyrin ring system at the relevant ring. Thus, the compounds of the invention include various groups as $R^4$, including substituents which provide additional porphyrin or porphyrin-related ring systems, as will be further described below.

$R^3$ in protoporphyrin-IX is 2-carboxyethyl (—CH$_2$CH$_2$COOH). However, the nature of $R^3$ (unless it contains a $\pi$-bond conjugated to ring $\pi$-bond), is ordinarily not relevant to the progress of the Diels-Alder reaction or to the effectiveness of the resulting product. $R^3$ can thus be, for example, lower alkyl (1–4C), or $\omega$-carboxyalkyl (2–6C) or the esters or amides thereof. The $R^3$ substituent may also be substituted with halogen as above-defined, or with other nonreactive substituents. However, as the convenient starting materials for the Gp compounds of the invention are the naturally occurring porphyrins, the preferred substituents for $R^3$ are —CH$_2$CH$_2$COOH or —CH$_2$CHR$_2$COOR, wherein R is alkyl (1–6C).

The hydro-monobenzoporphyrins which directly result from the Diels-Alder reaction described in the cited references can also be isomerized to compounds of formulas shown as 3 and 4 of FIG. 1. The depictions of compounds 3 and 4 in FIG. 1 do not show the relative position of the exocyclic methyl group (ring A of formula 3 and ring B of formula 4) with respect to the $R^2$ substituent. Either isomer is available.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1–4.

The description set forth above with respect to the compounds of formulas 1 and 2 concerning derivatization by conversion of the remaining vinyl substituent ($R^4$) and with respect to variability of —$R^3$ applies as well to the compounds of formulas 3, 4, 5 and 6.

In the BPD compounds of the invention, it has been found advantageous to hydrolyze or partially hydrolyze the esterified carboxy group in —CH$_2$CH$_2$COOR. The hydrolysis occurs at a much faster rate than that of the ester groups of $R^1$, $R^2$, and the solubility and biodistribution characteristics of the resulting compounds are more desirable than those of the unhydrolyzed form. Hydrolysis results in the diacid or monoacid products (or their salts).

The compounds of formulas 3 and 4 (BPD), and especially those which have hydrolyzed and partially hydrolyzed carbalkoxy groups in $R^3$, are most preferred. Compounds of the invention which contain —COOH may be prepared as the free acid or in the form of salts with organic or inorganic bases.

FIG. 2 shows four particularly preferred compounds of the invention. These compounds are collectively designated benzoporphyrin derivative (BPD) as they are forms of Gp having the formula 3 or 4. These are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is $—CH_2CH_2COOR^{3'}$. As shown in FIG. 2, each $R^{3'}$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl (1-6C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolyzates. In addition, mixtures of any two or more of BPD-MA, -MB, -DA and -DB may be employed in the method of the invention.

It will be noted that many of the compounds of FIG. 1 contain at least one chiral center and therefore exist as optical isomers. The method of the invention can employ compounds having both configurations of the chiral carbons, whether the compounds are supplied as isolates of a single stereoisomer or are mixtures of enantiomers and/or diastereomers. Separation of mixtures of diastereomers may be effected by any conventional means; mixtures of enantiomers may be separated by usual techniques of reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods of therapy and diagnosis set forth herein.

Generally, and in summary with respect to substituents, each $R^1$ and $R^2$ is independently selected from the group consisting of carbalkoxy (2-6C), alkyl (1-6C) sulfonyl, aryl (6-10C) sulfonyl, aryl (6-10C); cyano; and $—CONR^5CO—$ wherein $R^5$ is aryl (6-10C) or alkyl (1-6C);

each $R^3$ is independently ω-carboxyalkyl (2-6C) or a salt, amide, ester or acylhydrazone thereof, or is alkyl (1-6C); and $R^4$ is vinyl, $CHCH_2$, $CHOR^{4'}$, $—CHO$, $—COOR^{4'}$, $CH(OR^{4'})CH_3$, $CH(OR^{4'})CH_2OR^{4'}$, $—CH(SR^{4'})CH_3$, $—CH(NR^{4'})CH_3$, $—CH(CN)CH_3$, $—CH(COOR^{4'})CH_3$, $—CH((OOCR^{4'})CH_3$, $—CH(halo)CH_3$, or $—CH(halo)CH_2(halo)$, wherein $R^{4'}$ is H, alkyl (1-6C) optionally substituted with a hydrophilic substituent, or wherein $R^4$ is an organic group of <12C resulting from direct or indirect derivatization of vinyl, or wherein $R^4$ is a group containing 1-3 tetrapyrrole-type nuclei of the formula $—L—P$ as herein defined.

Compounds of the formulas 3 and 4 and mixtures thereof are particularly preferred. Also preferred are those wherein $R^1$ and $R^2$ are the same and are carbalkoxy, especially carboethoxy; also preferred are those wherein $R^4$ is $—CHCH_2$, $CH(OH)CH_3$ or $—CH(halo)CH_3$, or is a group containing 1-3 tetrapyrrole-type nuclei of the formula $—L—P$ (defined below).

As used herein, "tetrapyrrole-type nucleus" represents a four-ring system of the skeleton:

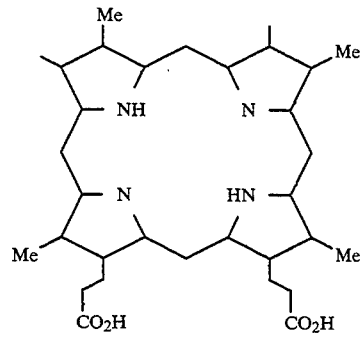

and a salt, ester, amide or acylhydrazone thereof, which is highly conjugated. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

One group of compounds is that wherein the substituent $R^4$ includes at least one additional tetrapyrrole-type nucleus. The resulting compounds of the invention are dimers or oligomers in which at least one of the tetrapyrrole-type ring systems is Gp. Linkage between the Gp moiety through the position of $R^4$ to an additional tetrapyrrole-type ring system may be through an ether, amine or vinyl linkage. Additional derivatization in the case of porphyrin ring systems which have two available substituent positions (in both A and B rings) corresponding to $R^4$ can also be formed, as further described below.

As stated above, the compounds of formulas shown in FIG. 1 include those wherein the embodiment of $R^4$ is formed by addition to the vinyl groups of initial Gp products. Thus, $R^4$ can be any substituent consistent with that formed by a facile addition reaction. Thus, both added substituents can be, for example, OH or halo, and these substituents can be further substituted, or the addition reagent may be of the form HX wherein H is added to the ring-adjacent carbon to provide $R^4$ of the form

—CHCH₃
|
X

The vinyl group can also be oxidized to obtain R⁴ as CH₂OH, —CHO, or COOH and its salts and esters.

Thus, in general R⁴ represents any substituents to which the vinyl group —CH=CH₂ is readily converted by cleavage or addition, and further resultants of reaction of leaving groups with additional moieties. Typical R⁴ substituents include: CH(OH)Me, —CHBrMe, —CH(OMe)Me, —CH(pyridinum bromide)Me, —CH(SH)Me and the disulfide thereof, —CHOHCH₂OH, —CHO, and —COOH or —COOMe.

When R⁴ is —L—P, the substituent formula "—L—P" represents a substituent wherein —L— is selected the group consisting of

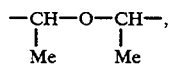  (a)

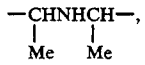  (b)

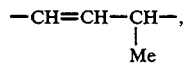  (c)

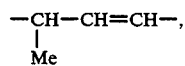  (d)

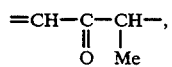  (e)

and

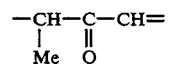  (f)

and P is selected from the group consisting of Gp wherein Gp is of the formula 1-6 shown in FIG. 1, but lacking R⁴ and conjugated through the position shown in FIG. 5 as occupied by R⁴ to L, and a porphyrin.

(It is also understood that when —L— is of the formula (e) or (f), the ring system to which the double bond is attached will have a resonance system corresponding to

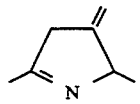

in the ring to which the double bond is attached, as shown.)

The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert to the corresponding green porphyrin.

DETAILED DESCRIPTION OF THE METHOD

In the method of the invention, the subject is administered an amount of the Gp compound or a mixture of Gp compounds in one or several dosages. Suitable amounts for total dosage are in the range of 0.04-20 mg/kg body weight; preferably 0.2-8 mg/kg body weight. Typical amounts per dose are in the range of 0.01-5 mg/kg or preferably 0.05-2 mg/kg. These dosage ranges are intended to be suggestive and not limiting, since of course the individual reactions of particular subjects will vary. Adjustment of the dosage ranges in accordance with these variations is routine among practitioners.

Similarly, no single protocol is desirable for all cases. However, typical protocols will include an initial dose administered within six hours before or after the angioplasty procedure followed by 1-4 additional doses at weekly, biweekly or monthly intervals. Again, these protocols are not intended to be limiting in view of the wide variation in protocol design permitted.

The Gp of the invention may be administered as a single compound, preferably BPD-MA, or as mixtures of various Gps. Suitable formulations include those appropriate for systemic administration, including preparations for injection, transmucosal or transdermal administration, or even oral administration. A particularly preferred means of formulating the Gp of the invention for this use is in the form of liposomes. The Gp may be included within the liposomes, attached to their surface, or both. Suitable methods for preparing liposomes are well known in the art, and inclusion of Gp in such preparations is described in U.S. Pat. No. 5,214,036 and U.S. patent application Ser. No. 07/832,542 filed 15 Mar. 1993, both of which are incorporated herein by reference. As stated above, the Gp compounds and formulations are administered without the necessity of irradiating the site of potential restenosis with light absorbed by the Gp. By "in the absence of irradiation with light absorbed by said Gp" is meant that no such deliberate irradiation is administered. The phrase does not, of course, exclude inadvertent, coincidental, or normal exposure of the affected tissues to light.

The following examples are intended to illustrate but not to limit the invention.

EXAMPLE 1

Prevention of Restenosis in Rabbits

Two groups of eight rabbits each were induced to an atherosclerotic state by an atherogenic diet and balloon-stretch injury of the aorta as described previously Johnson, et al. *Laser Research in Medicine* (1987) 10:13-17. The experimental group received 2 mg/kg BPD-MA intravenously at the time of the injury, and one, two and three months later; the control group received no drug. The smooth muscle cell proliferation and intimal hyperplasia was quantitated in both groups at four months by sacrificing the animals and comparing the magnitude of formation by microscopy. The results were evaluated as percentage of occlusion and thickness of the intimal hyperplasia. Percent occlusion used 6 diameters yielding 12 points on the vessel wall, in a clock-like format. Percent occlusion was calculated by the formula $$1 - \frac{\Sigma \text{ (plaque to plaque distance)}^2}{\Sigma \text{ (wall to wall distance)}^2} \times 100 = \% \text{ vessel closed.}$$

For intimal hyperplasia thickness, 12 measures were taken in a clock-like format and the average of 12 thickness measurements was computed.

On gross examination, the controls had diffuse IH throughout the aorta in seven out of eight animals. The experimental group had no IH in four out of eight animals, only one small area in three out of eight and a mild diffuse IH in one. When evaluated by microscopy, the mean IH thickness in the control group was $190\mu$ and in the experimental group $21\mu$; normal media thickness was $140\mu$. Lumen reduction by IH was 27% in the controls and only 3% in the BPD-treated rabbits. Media invasion and wall calcification were seen in six and five of the eight controls, respectively, but in none of the test animals. Smooth muscle cells were present in IH of all animals showing IH, and were dense in controls and less dense in BPD treated animals. Thus, BPD-MA markedly inhibits IH in this model.

We claim:

1. A method to inhibit the development of intimal hyperplasia following angioplasty which method comprises administering to a subject in conjunction with said angioplasty an amount of green porphyrin (Gp) effective to inhibit said development, and allowing said inhibition to occur in the absence of irradiation with light absorbed by said Gp.

2. The method of claim 1 wherein said administering is conducted by administering 2–5 doses, wherein the first said dose is administered within 6 hours of said angioplasty.

3. The method of claim 2 wherein said effective amount is 0.01–5 mg/kg in each dose.

4. The method of claim 3 wherein said effective amount is 0.05–2 mg/kg in each dose.

5. The method of claim 1 wherein said Gp is administered in a liposomal formulation.

6. The method of claim 1 wherein Gp is of the formula 1–6, as shown in FIG. 1, wherein $R^1$, $R^2$, $R^3$ and $R^4$ are non-interfering substituents.

7. The method of claim 6 wherein $R^1$ and $R^2$ are carbomethoxy and carboethoxy.

8. The method of claim 6 wherein each $R^3$ is —$CH_2CH_2COOH$ or a salt, amide, ester or acyl hydrazone thereof.

9. The method of claim 6 wherein Gp is of the formula 3 or 4, wherein $R^4$ is a non-interfering substituent.

10. The method of claim 9 wherein said Gp is selected from the group consisting of BPD-DA, BPD-DB, BPD-MA and BPD-MB.

11. The method of claim 10 wherein said Gp is BPD-MA.

12. A method to inhibit the development of intimal hyperplasia following angioplasty which method consists essentially of administering to a subject in conjunction with said angioplasty an amount of green porphyrin (Gp) effective to inhibit said development, and allowing said inhibition to occur in the absence of irradiation with light absorbed by said Gp.

13. The method of claim 12 wherein said administering is conducted by administering 2–5 doses, wherein the first said dose is administered within 6 hours of said angioplasty.

14. The method of claim 13 wherein said effective amount is 0.01–5 mg/kg in each dose.

15. The method of claim 14 wherein said effective amount is 0.05–2 mg/kg in each dose.

16. The method of claim 12 wherein said Gp is administered in a liposomal formulation.

17. The method of claim 12 wherein Gp is of the formula 1–6, as shown in FIG. 1, wherein $R^1$, $R^2$, $R^3$ and $R^4$ are non-interfering substituents.

18. The method of claim 17 wherein $R^1$ and $R^2$ are carbomethoxy and carboethoxy.

19. The method of claim 17 wherein each $R^3$ is —$CH_2CH_2COOH$ or a salt, amide, ester or acyl hydrazone thereof.

20. The method of claim 17 wherein Gp is of the formula 3 or 4, wherein $R^4$ is a non-interfering substituent.

21. The method of claim 20 wherein said Gp is selected from the group consisting of BPD-DA, BPD-DB, BPD-MA and BPD-MB.

22. The method of claim 21 wherein said Gp is BPD-MA.

* * * * *